United States Patent
Steiner

(10) Patent No.: US 6,300,343 B1
(45) Date of Patent: Oct. 9, 2001

(54) METHOD OF TREATMENT

(75) Inventor: Martin X. Steiner, Paoli, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/719,378
(22) PCT Filed: Jun. 16, 1999
(86) PCT No.: PCT/US99/13623
 § 371 Date: Dec. 11, 2000
 § 102(e) Date: Dec. 11, 2000
(87) PCT Pub. No.: WO99/65491
 PCT Pub. Date: Dec. 23, 1999

(30) Foreign Application Priority Data

Jun. 16, 1998 (GB) .................................................. 9812941

(51) Int. Cl.$^7$ .................................................. A61K 31/445
(52) U.S. Cl. .............................................................. 514/321
(58) Field of Search ............................................... 514/321

(56) References Cited

U.S. PATENT DOCUMENTS 4,721,723  1/1988  Barnes et al. .
5,371,092  12/1994  Johnson .

Primary Examiner—Raymond Henley, III
(74) Attorney, Agent, or Firm—Wayne J. Dustman

(57) ABSTRACT

The present invention is directed to a method for promoting somking cessation or reduction or preventing relapse smoking, comprising administering an effective, non-toxic amount of paroxetine or a pharmaceutically acceptable salt or solvate thereof, to a human in need thereof.

8 Claims, No Drawings

METHOD OF TREATMENT

This is a 371 of PCT/US99/13623, filed Jun. 16, 1999.

The present invention relates to a method for promoting smoking cessation or reduction or preventing relapse smoking, and especially to the use of paroxetine in such treatment.

Pharmaceutical products with antidepressant and anti-Parkinson properties are described in U.S. Pat. Nos. 3,912,743 and 4,007,196. An especially important compound among those disclosed is paroxetine, the (−) trans isomer of 4-(4'-fluorophenyl)-3-(3',4'-methylenedioxyphenoxymethyl)-piperidine (see Example 2 of U.S. Pat. No. 4,007,196). This compound is a Selective Serotonin Reuptake Inhibitor (SSRI). The hydrochloride salt of paroxetine is approved for human use in therapy to treat inter alia depression, obsessive compulsive disorder (OCD) and panic.

In commercial use, paroxetine hydrochloride is supplied as a crystalline hemihydrate (see EP-A-0223403 of Beecham Group). Various crystalline anhydrate forms are also known (see WO96/24595 of SmithKline Beecham plc).

SSRI compounds such as fluoxetine and sertraline have been proposed for use in treating chemical dependency (see U.S. Pat. No. 5,130,338) including nicotine withdrawal symptons (see U.S. Pat. No. 4,940,585 and 4,999,382). However various clinical studies have suggested that while fluoxetine had favourable influences on factors associated with smoking cessation such as weight gain and alcohol consumption, it did not enhance smoking cessation rates (see Mizes et al, Psychopharmacol.Bull. 32, No.3, 491, 1996; Sullivan et al, J.Clin.Pharmacol. 29, No.9, 850, 1989).

It has now been surprisingly discovered that paroxetine has potential therapeutic utility as a medicament for promoting smoking cessation or reduction or preventing relapse smoking.

Accordingly, the present invention provides a method for promoting smoking cessation or reduction or preventing relapse smoking, which method comprises administering an effective, non-toxic amount of paroxetine or a pharmaceutically acceptable salt or solvate there of, to human in need thereof.

The present invention also provides the use of paroxetine or a pharmaceutically acceptable salt or solvate thereof in the manufacture of a medicament for use in promoting smoking cessation or reduction or preventing relapse smoking.

Paroxetine used in the present invention is suitably in the form of the free base or a pharmaceutically acceptable salt thereof. A preferred pharmaceutically acceptable salt of paroxetine is crystalline hydrochloride. Suitable procedures for preparing paroxetine hydrochloride include those mentioned in U.S. Pat. Nos. 4,009,196, 4,721,723, 4,902,801, 4,861,893 and 5,039,803 and PCT/GB93/00721. Especially preferred is the hemi-hydrate, prepared as EP-A-0223403.

A medicament, for use in promoting smoking cessation or reduction or preventing relapse smoking may be prepared by admixture of paroxetine or a pharmaceutically acceptable salt or solvate thereof with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use in promoting smoking cessation or reduction or preventing relapse smoking.

The suitable dosage range for paroxetine or a pharmaceutically acceptable salt or solvate depends on the severity of the smoking disorders and on the condition of the patient. It will also depend, inter alia, upon the relation of potency to absorbability and the frequency and route of administration.

Paroxetine or a pharmaceutically acceptable salt or solvate thereof may be formulated for administration by any route, and examples are oral, sub-lingual, rectal, topical, trans-dermal, parenteral, intravenous or intramuscular administration. Preparations may, if desired, be designed to give slow release of the paroxetine or a pharmaceutically acceptable salt or solvate thereof. The medicaments may additionally contain other active ingredients useful in methods of promoting smoking cessation or reduction or preventing relapse smoking, such as nicotine or a pharmaceutically acceptable derivative thereof.

The medicaments may, for example, be in the form of tablets, capsules, sachets, vials, powders, granules, lozenges, reconstitutable powders, or liquid preparations, for example solutions or suspensions, or suppositories.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute paroxetine or a salt or solvate thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing paroxetine or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Paroxetine or a pharmaceutically acceptable salt or solvate thereof may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned hereinbefore, the effective dose of the paroxetine or pharmaceutically acceptable salt or solvate depends on the severity of the smoking disorders to be treated, the condition of the patient and on the frequency and route of administration. A unit dose will generally contain from 2 to 1000 mg and preferably will contain from 30 to 500 mg, in particular 20, 50, 100, 150, 200, 250, 300, 350, 400, 450, or 500 mg. The composition may be administered once or more times a day, for example 2, 3 or 4 times daily, and the total daily dose for a 70 kg adult will normally be in the range 100 to 3000 mg. Preferably the unit dose will contain from 2 to 20 mg of paroxetine (calculated as free base) and be administered in multiples, if desired, to give the preceding daily dose.

Preferably the present invention is practised using a controlled release or delayed release formulation containing paroxetine or a pharmaceutically acceptable salt thereof.

By controlled release is meant any formulation technique wherein release of the active substance from the dosage from is modified to occur at a slower rater than that from an immediate release product, such as a conventional swallow tablet or capsule.

By delayed release is meant any formulation technique wherein release of the active substance from the dosage form is modified to occur at a later time than that from a conventional immediate release product. The subsequent release of active substance from a delayed release formulation may also be controlled as defined above.

Examples of controlled release formulations which are suitable for incorporating paroxetine are described in:

Sustained Release Medications, Chemical Technology Review No. 177. Ed. J. C. Johnson. Noyes Data Corporation 1980.

Controlled Drug Delivery, Fundamentals and Applications, 2nd Edition. Eds. J. R. Robinson, V. H. L. Lee. Mercel Dekkes Inc. New York 1987.

Examples of delayed release formulations which are suitable for incorporating paroxetine are described in:

Remington's Pharmaceutical Sciences 16th Edition, Mack Publishing Company 1980, Ed. A. Osol.

Such controlled release formulations are preferably formulated in a manner such that release of active substance such as paroxetine is effected predominantly during the passage through the stomach and the small intestine, and delayed release formulations are preferably formulated such that release of active substance such as paroxetine is avoided in the stomach and is effected predominantly during passage through the small intestine Said formulations are preferably formulated such that the release of the active substance is predominantly 1½ to 3 hours post ingestion.

Preferred formulations are ultimately enteric coated tablets or caplets, wax or polymer coated tablets or caplets or time-release matrices, or combinations thereof.

Particularly preferred formulations are described in U.S. Pat. No. 5,102,666.

Thus, a particular aspect of the invention involves use of a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerised repeating unit and cross-linking agent, respectively, with (2) water, in the presence of paroxetine. The amount of calcium polycarbophil present is from about 0.1 to about 99% by weight, for example about 10%. The amount of active agent present is from about 0.0001 to about 65% by weight, for example between about 5 and 20%. The amount of water present is from about 5 to about 200% by weight, for example between about 5 and 10%. The interaction is carried out at a pH of between about 3 and about 10, for example about 6 to 7. The calcium polycarbophil is originally present in the form of a calcium salt containing from about 5 to about 25% calcium.

Further particularly preferred formulations are described in U.S. Pat. No. 5,422,123.

Thus, a further particular aspect involves use of a system for the controlled release of paroxetine, comprising (a) a deposit-core comprising an effective amount of paroxetine and having defined geometric form, and (b) a support-platform applied to said deposit-core, wherein said deposit-core contains paroxetine, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

The present invention further provides a pharmaceutical composition for use in promoting smoking cessation or reduction or preventing relapse smoking which comprises an effective amount of paroxetine or a pharmaceutically acceptable salt or solvate thereof and a pharmaceutically acceptable carrier. Such compositions may be prepared in the manner as hereinbefore described.

The paroxetine product of the present invention may optionally be coadministered with a nicotine-containing smoking cessation aid such as a patch, gum, or inhalator.

The following Examples disclose suitable pharmaceutical compositions for use in the present invention.

EXAMPLE 1

(Hydrophilic Matrix)

|  | % w/w |
|---|---|
| Intragranular |  |
| Paroxetine Hydrochloride | 11.45 |
| Methocel E5 | 1.25 |
| Lactose | 12.3 |
| Extragranular |  |
| Methocel K100LV | 30.0 |
| Lactose | 44.0 |
| Magnesium Stearate | 1.0 |
| TOTAL | 100.0 |

EXAMPLE 2

(Hydrophilic Matrix)

|  | % w/w |
|---|---|
| Intragranular |  |
| Paroxetine Hydrochloride | 11.45 |
| Methocel E5 | 1.25 |
| Lactose | 12.3 |
| Extragranular |  |
| Methocel K100LV | 27.5 |
| Methocel K4M | 7.5 |
| Lactose | 39.0 |
| Magnesium Stearate | 1.0 |
| TOTAL | 100.0 |

EXAMPLE 3

(pH Sensitive Coat on Immediate Release Core)

|  | % w/w |
|---|---|
| Tablet Core |  |
| Paroxetine Hydrochloride | 11.45 |
| Lactose | 64.05 |
| Microcrystalline Cellulose | 20.0 |
| Sodium Starch Glycollate | 4.0 |
| Magnesium Stearate | 0.5 |
| TOTAL | 100.0 |
| Tablet Coating |  |
| (apply approximately 6–10% of tablet core weight) |  |
| Hydroxypropylmethylcellulose Phthalate | 90.0 |
| Triacetin | 10.0 |

EXAMPLE 4

(pH Sensitive Coat on Immediate Release Core)
Tablet Core as in Example 3

|  | % w/w |
|---|---|
| Tablet Coating |  |
| (apply approximately 6–10% of tablet core weight) |  |
| Cellulose Acetate Phthalate | 90.0 |
| Diethyl Phthalate | 10.0 |

EXAMPLE 5

(Controlled Release Coating on Immediate Release Core)
Tablet Core as in Example 3

|  | % w/w |
|---|---|
| Tablet Coating |  |
| (apply approximately 5–12% of tablet core weight) |  |
| Eudragit RS 100 | 86.0 |
| Dibutyl Phthalate | 10.0 |
| Talc | 4.0 |
| FD&C Yellow No. 6 | 0.01 |

EXAMPLE 6

(pH Sensitive Coat on Controlled Release Core.)
Tablet Core as in Example 3
Tablet Coating as in Example 3

EXAMPLE 7

(Encapsulated Controlled Release Coated Beads)

|  | % w/w (approx) |
|---|---|
| Pellet |  |
| Non Pareil Seed | 30 |
| Paroxetine Hydrochloride | 40 |
| Gelatin | 8 |
| Lactose | 20 |

| | -continued | |
|---|---|---|
| Talc | | 2 |

| | % w/w |
|---|---|
| Coating | |
| Glycerylmonostearate | 36.6 |
| Glyceryldistearate | 53.4 |
| White Wax | 10.0 |

EXAMPLE 8

(Controlled Release Bilayer Tablet)

| Component | mg/tablet | Function |
|---|---|---|
| Active Layer | | |
| Paroxetine Hydrochloride | 22.89* | Active |
| Methocel K4M | 15.00 | Hydrogel polymer |
| Lactose monohydrate | 62.0 | Hydrophilic agent |
| Polyvinylpyrrolidone | 3.0 | Binder |
| Magnesium stearate | 1.0 | Hydrophobic agent |
| Syloid 244 | 1.0 | Hydrophilic agent |
| Support platform | | |
| Compritol 888 | 15.04 | Plasticizer |
| Lactose monohydrate | 29.32 | Hydrophilic agent |
| Polyvinylpyrrolidone | 4.0 | Binder |
| Magnesium stearate | 1.52 | Hydrophobic agent |
| Methocel E5 | 29.32 | Hydrogel polymer |
| Iron oxide | 0.08 | Colourant |
| Total tablet weight | 184.89 mg | |

*Equivalent to 20 mg paroxetine as free base.

The powder blend for each layer was wet granulated in a high shear mixer/granulator and dried in a fluid bed drier. The bilayer tablets were compressed on a Manesty triple layer press.

EXAMPLE 9

(Enteric Coated Calcium Polycarbophil Formulation)

| Component | mg/tablet | Function |
|---|---|---|
| Core | | |
| Paroxetine Hydrochloride | 22.89* | Active |
| Calcium polycarbophil | 20.00 | Matrix |
| Lactose anhydrous | 146.11 | Hydrophilic agent/diluent |
| Polyvinylpyrrolidone | 10.0 | Binder |
| Magnesium stearate | 1.0 | Hydrophobic agent/lubricant |
| Water** | 0.024 | Granulating liquid |
| Enteric coat | | |
| Eudragit | 22.19 | Polymer |
| Talc | 1.53 | Lubricant |
| Triethyl citrate | 1.00 | Plasticizer |
| Water** | 24.6 | Diluent |
| Film coat | | |
| Opadry pink | 10.5 | Film coat |
| Water** | 94.5 | Diluent |

| Component | mg/tablet | Function |
|---|---|---|
| Polish coat | | |
| Opadry clear | 0.750 | |
| Water** | 29.3 | Diluent |

*Equivalent to 20 mg paroxetine as free base.
**Removed during processing.

The core constituents were wet granulated in a high shear mixer/granulator, and dried in a fluid bed drier. The magnesium stearate was then added and the mixture processed in a low shear mixer. The mix was then compressed on a B type rotary tablet press. Coating was carried out using an Accela cota.

EXAMPLE 10

(Controlled Release Bilayer Tablet)

| Component | mg/tablet | Function |
|---|---|---|
| Active Layer | | |
| Paroxetine Hydrochloride | 22.89* | Active |
| Methocel K4M | 20.00 | Hydrogel polymer |
| Lactose monohydrate | 60.0 | Hydrophilic agent |
| Polyvinylpyrrolidone | 5.0 | Binder |
| Magnesium stearate | 1.0 | Hydrophobic agent |
| Syloid 244 | 1.0 | Hydrophilic agent |
| Support platform | | |
| Compritol 888 | 14.72 | Plasticizer |
| Lactose monohydrate | 30.60 | Hydrophilic agent |
| Polyvinylpyrrolidone | 2.80 | Binder |
| Magnesium stearate | 0.80 | Hydrophobic agent |
| Methocel E5 | 30.60 | Hydrogel polymer |
| Syloid 244 | 0.40 | Hydrophilic agent |
| Iron oxide | 0.08 | Colourant |
| Total tablet weight | 189.89 mg | |

*Equivalent to 20 mg paroxetine as free base.
The process was as described in Example 8.

EXAMPLE 11

(Controlled Release Bilayer Tablet)

| Component | mg/tablet | Function |
|---|---|---|
| Active Layer | | |
| Paroxetine Hydrochloride | 22.89 | Active |
| Methocel K4M | 15.00 | Hydrogel poymer |
| Lactose monohydrate | 63.31 | Hydrophilic agent |
| Polyvinylpyrrolidone | 2.0 | Binder |
| Magnesium stearate | 1.0 | Hydrophobic agent |
| Syloid 244 | 0.40 | Hydrophilic agent |
| Support platform - as in Example 10. | | |
| Total tablet weight | 184.60 mg | |

The process was as described in Example 8.

EXAMPLE 12
(Enteric Coated Controlled Release Bilayer Tablet)

| Component | mg/tablet | Function |
|---|---|---|
| Active Layer | | |
| Paroxetine Hydrochloride | 28.61* | Active |
| Methocel K4M | 18.75 | Hydrogel polymer |
| Lactose monohydrate | 79.14 | Hydrophilic agent |
| Polyvinylpyrrolidone | 2.50 | Binder |
| Magnesium stearate | 1.25 | Hydrophobic agent |
| Syloid 244 | 0.50 | Hydrophilic agent |
| Support platform | | |
| Compritol 888 | 15.04 | Plasticizer |
| Lactose monohydrate | 30.50 | Hydrophilic agent |
| Polyvinylpyrrolidone | 4.00 | Binder |
| Magnesium stearate | 0.80 | Hydrophobic agent |
| Methocel E5 | 29.32 | Hydrogel polymer |
| Syloid 244 | 0.32 | Hydrophilic agent |
| Iron oxide | 0.02 | Colourant |
| Enteric coating | | |
| Eudragit | 13.27 | Polymer |
| Talc | 3.31 | Lubricant |
| Triethyl citrate | 1.33 | Plasticizer |
| Water** | 36.25 | Diluent |
| Total tablet weight | 228.66 mg | |

The process was as described in Example 9.

EXAMPLE 13

The following are mixed together in a conventional manner and compressed into tablets of ca. 300 mg weight containing ca. 20 mg of paroxetine (calculated as the free base).

| | |
|---|---|
| Paroxetine hydrochloride hemihydrate | 228.8 g |
| Dibasic calcium phosphate dihydrate | 2441.2 g |
| Hydroxypropylmethyl cellulose 2910 | 150.0 g |
| Sodium starch glycollate | 150.0 g |
| Magnesium Stearate | 30.0 g |
| Total tablet weight | 3000.0 g |

What is claimed is:

1. A method for promoting smoking cessation or reduction or preventing relapse smoking, which method comprises administering an effective amount of paroxetine or a pharmaceutically acceptable salt or solvate there of, to a human in need thereof.

2. The method according to claim 1 wherein the paroxetine is in the form of the free base or a pharmaceutically acceptable salt thereof.

3. The method according to claim 2 wherein the pharmaceutically acceptable salt of paroxetine is a crystalline hydrochloride.

4. The method according to claim 3 wherein the hydrochloride is the hemi-hydrate.

5. The method according to claim 1 wherein the paroxetine is administered in a controlled release or delayed release formulation.

6. The method according to claim 5 wherein the paroxetine is administered orally.

7. The method according to claim 6 wherein the controlled release or delayed release formulation comprises (a) a deposit-core comprising an effective amount of paroxetine and having defined geometric form, and (b) a support-platform applied to said deposit-core, wherein said deposit-core contains paroxetine, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

8. The method according to claim 1 wherein the paroxetine is coadministered with a nicotine-containing smoking cessation aid.

\* \* \* \* \*